(12) United States Patent
Melville et al.

(10) Patent No.: US 9,894,329 B2
(45) Date of Patent: Feb. 13, 2018

(54) SCANNING LASER PROJECTION DISPLAY FOR SMALL HANDHELD DEVICES

(71) Applicant: University of Washington, Seattle, WA (US)

(72) Inventors: Charles D. Melville, Issaquah, WA (US); Richard S. Johnston, Sammamish, WA (US); Cameron M. Lee, Seattle, WA (US); Eric J. Seibel, Seattle, WA (US); Brian T. Schowengerdt, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 14/863,276

(22) Filed: Sep. 23, 2015

(65) Prior Publication Data
US 2016/0014383 A1    Jan. 14, 2016

Related U.S. Application Data

(60) Continuation of application No. 14/275,436, filed on May 12, 2014, now Pat. No. 9,182,655, which is a
(Continued)

(51) Int. Cl.
*H04N 9/31* (2006.01)
*A61B 1/00* (2006.01)
(Continued)

(52) U.S. Cl.
CPC ......... *H04N 9/3135* (2013.01); *A61B 1/0008* (2013.01); *A61B 1/00172* (2013.01);
(Continued)

(58) Field of Classification Search
CPC ........ G02F 1/00; G02F 1/0018; G02F 1/0081; G02F 1/01; G02F 1/0102; G02F 1/0105; G02F 1/011; G02F 1/0115; G02F 1/3558; G02F 1/365; G02F 1/377; G02F 2201/30; G09F 9/305; G09F 9/00
(Continued)

(56) References Cited

U.S. PATENT DOCUMENTS 5,727,098 A * 3/1998 Jacobson ............. G02B 26/103
385/22
6,046,720 A    4/2000 Melville et al.
(Continued)

*Primary Examiner* — Francis M Legasse, Jr.
(74) *Attorney, Agent, or Firm* — Wilson Sonsini Goodrich & Rosati

(57) ABSTRACT

Image projection devices, high-speed fiber scanned displays and related methods for projecting an image onto a surface and interfacing with the projected image are provided. A method for projecting one or more images and obtaining feedback with an optical input-output assembly is provided. The input-output assembly comprising a light-scanning optical fiber and a sensor. The method includes generating a sequence of light in response to one or more image representations and a scan pattern of the optical fiber, articulating the optical fiber in the scan pattern, projecting the sequence of light from the articulated optical fiber, and generating a feedback signal with the sensor in response to reflections of the sequence of light.

20 Claims, 14 Drawing Sheets

Related U.S. Application Data division of application No. 12/468,832, filed on May 19, 2009, now Pat. No. 8,757,812.

(60) Provisional application No. 61/054,428, filed on May 19, 2008.

(51) Int. Cl.

| | | |
|---|---|---|
| *A61B 1/07* | (2006.01) | |
| *G03B 21/00* | (2006.01) | |
| *G02B 26/10* | (2006.01) | |
| *A61B 5/00* | (2006.01) | |
| *G02B 6/26* | (2006.01) | |
| *A61B 1/06* | (2006.01) | |
| *G03B 21/20* | (2006.01) | |

(52) U.S. Cl.
CPC .............. *A61B 1/07* (2013.01); *G02B 26/103* (2013.01); *G03B 21/00* (2013.01); *H04N 9/3129* (2013.01); *H04N 9/3173* (2013.01); *A61B 1/00165* (2013.01); *A61B 1/0638* (2013.01); *A61B 5/0062* (2013.01); *G02B 6/262* (2013.01); *G03B 21/20* (2013.01)

(58) Field of Classification Search
USPC ........ 250/221, 234–236, 216, 227.11, 227.2, 250/227.21; 353/30, 31, 46, 50, 98, 99, 353/121, 122; 385/25, 31, 15
See application file for complete search history.

(56) References Cited

U.S. PATENT DOCUMENTS

| | | |
|---|---|---|
| 7,159,782 B2 | 1/2007 | Johnston et al. |
| 7,189,961 B2 | 3/2007 | Johnston et al. |
| 7,298,938 B2 | 11/2007 | Johnston |
| 7,312,879 B2 | 12/2007 | Johnston |
| 7,369,584 B2 | 5/2008 | Goldman et al. |
| 7,395,967 B2 | 7/2008 | Melville |
| 8,757,812 B2 | 6/2014 | Melville et al. |
| 9,182,655 B2 | 11/2015 | Melville et al. |
| 2006/0072843 A1 | 4/2006 | Johnston |
| 2006/0226231 A1 | 10/2006 | Johnston |
| 2007/0195294 A1* | 8/2007 | Willey ................ G03B 21/26 353/119 |
| 2007/0285629 A1 | 12/2007 | Yavid |
| 2008/0218824 A1 | 9/2008 | Johnston |
| 2009/0218641 A1 | 9/2009 | Melville |
| 2015/0281630 A1 | 10/2015 | Melville et al. |

* cited by examiner

SCANNING LASER PROJECTION DISPLAY FOR SMALL HANDHELD DEVICES

CROSS-REFERENCE

This application is a Continuation application of U.S. application Ser. No. 14/275,436, filed May 12, 2014, now U.S. Pat. No. 9,182,655, which is a Divisional application of U.S. application Ser. No. 12/468,832, filed May 19, 2009, now U.S. Pat. No. 8,757,812, which claims the benefit of U.S. Provisional Application No. 61/054,428, filed May 19, 2008, entitled "Scanning Laser Projection Display for Small Handheld Devices," the full disclosures of which are incorporated herein by reference in their entirety.

BACKGROUND

The present invention relates generally to image projection devices, and more specifically to high-speed fiber scanned displays and related methods for projecting an image onto a surface and, in some embodiments, interfacing with the projected image.

The increasing computational power and connectivity of mobile devices, such as cell phones, video iPods, and PDAs, have enabled mobile internet access and playback of images and video. Presently, many such electronic devices include a built in video display, which impacts the size and cost of the device. For example, a typical hand held gaming device includes a display that is sufficiently large to display enough information, as well as provide an image suitable for visual enjoyment.

Projectors using LCD panels as imaging elements are reasonably low cost, but are not energy efficient. To create dark pixels in the projected image, LCD panels block a portion of the light energy generated by the source from reaching the screen, so dark images require as much energy to project as bright images, placing an additional drain on the limited battery capacity of mobile devices. Furthermore, the maximum resolution of the projector is constrained by the size of the LCD panel and the attainable pixel pitch. In order to increase resolution, the dimensions of the LCD panel in the mobile device must be increased proportionately.

Holographic projectors can provide the advantage of lowered power consumption, as the majority of the light generated by the laser sources reaches the screen. However, holographic image generation requires complex processing, placing high computational demands on mobile devices with small, low-voltage processors, and the resolution of the projected image is also ultimately dependent on the size and pixel pitch of the spatial light modulator used to generate the holographic image.

The size and cost of mobile electronic devices is also influenced by input features. Existing mobile devices may include a number of input features, for example, input keys, touch screens, and the like. The input features employed with any particular mobile device can also have a significant influence on the level of functionality provided.

While many existing mobile electronic devices provide a good bit of functionality for their size and/or cost, further improvements in size, cost, and/or functionality are desirable. Thus, a need exists for improved image display and improved input features, which can be employed in various devices, for example, mobile electronic devices.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In many embodiments, improved methods, devices, and systems for projecting an image are provided. In many embodiments, methods, devices and systems for projecting an image and generating feedback via the projected image are provided. In many embodiments, such methods, devices, and systems include an articulated fiber assembly from which a sequence of light is projected to form an image, and in some embodiments, include a sensor for measuring reflections from the projected sequence of light. The use of the disclosed articulated fiber based projection, and projection and feedback, may provide for more compact display and feedback functionality, which can be employed in a range of electronic devices, for example, mobile electronic devices. In many embodiments, the combination of projection and feedback provides for combined input and output functionality via a compact device, which may be used to provide for increased functionality while simultaneously reducing relative size, weight, and cost.

In one aspect, a method for projecting one or more images with a projection device comprising a light-scanning optical fiber is provided. The method includes generating a sequence of light in response to one or more image representations and a scan pattern of the optical fiber, articulating the optical fiber in the scan pattern, and projecting the sequence of light from the articulated optical fiber. The articulated optical fiber is scanned within a within a Q factor of a resonant frequency of the optical fiber.

In another aspect, a method for projecting one or more images and obtaining feedback with an optical input-output assembly is provided. The input-output assembly comprising a light-scanning optical fiber and a sensor. The method includes generating a sequence of light in response to one or more image representations and a scan pattern of the optical fiber, articulating the optical fiber in the scan pattern, projecting the sequence of light from the articulated optical fiber, and generating a feedback signal with the sensor in response to reflections of the sequence of light.

In another aspect, a system for projecting one or more images is provided. The system includes a projection device comprising a light-scanning optical fiber, a laser assembly coupled with the light-scanning optical fiber and operable to generate the sequence of light, and a processor coupled with the light-scanning assembly and the laser assembly. The projection device is operable to project a sequence of light from the light-scanning fiber according to a scan pattern. The processor comprises a tangible medium comprising instructions that when executed cause the processor to generate the sequence of light in response to one or more image representations and the scan pattern, and provide control signals to the laser assembly and the light-scanning assembly to project the sequence of light according to the scan pattern.

In another aspect, a system for projecting one or more images and obtaining feedback is provided. The system includes a projection assembly comprising a light-scanning optical fiber, a sensor operable to measure reflections from light projected by the light-scanning optical fiber and generate a feedback signal corresponding thereto, a laser assembly coupled with the light-scanning optical fiber and operable to generate the sequence of light, and a processor coupled with the light-scanning assembly, the sensor, and the laser assembly. The projection assembly is operable to project a sequence of light from the light-scanning optical fiber according to a scan pattern. The processor comprises a tangible medium comprising instructions that when executed cause the processor to determine the sequence of light in response to one or more image representations and the scan pattern, provide control signals to the laser assembly and the light-scanning assembly to project the sequence of light from the light-scanning optical fiber according to the scan pattern, and receive a feedback signal generated by the sensor in response to reflections of the sequence of light.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
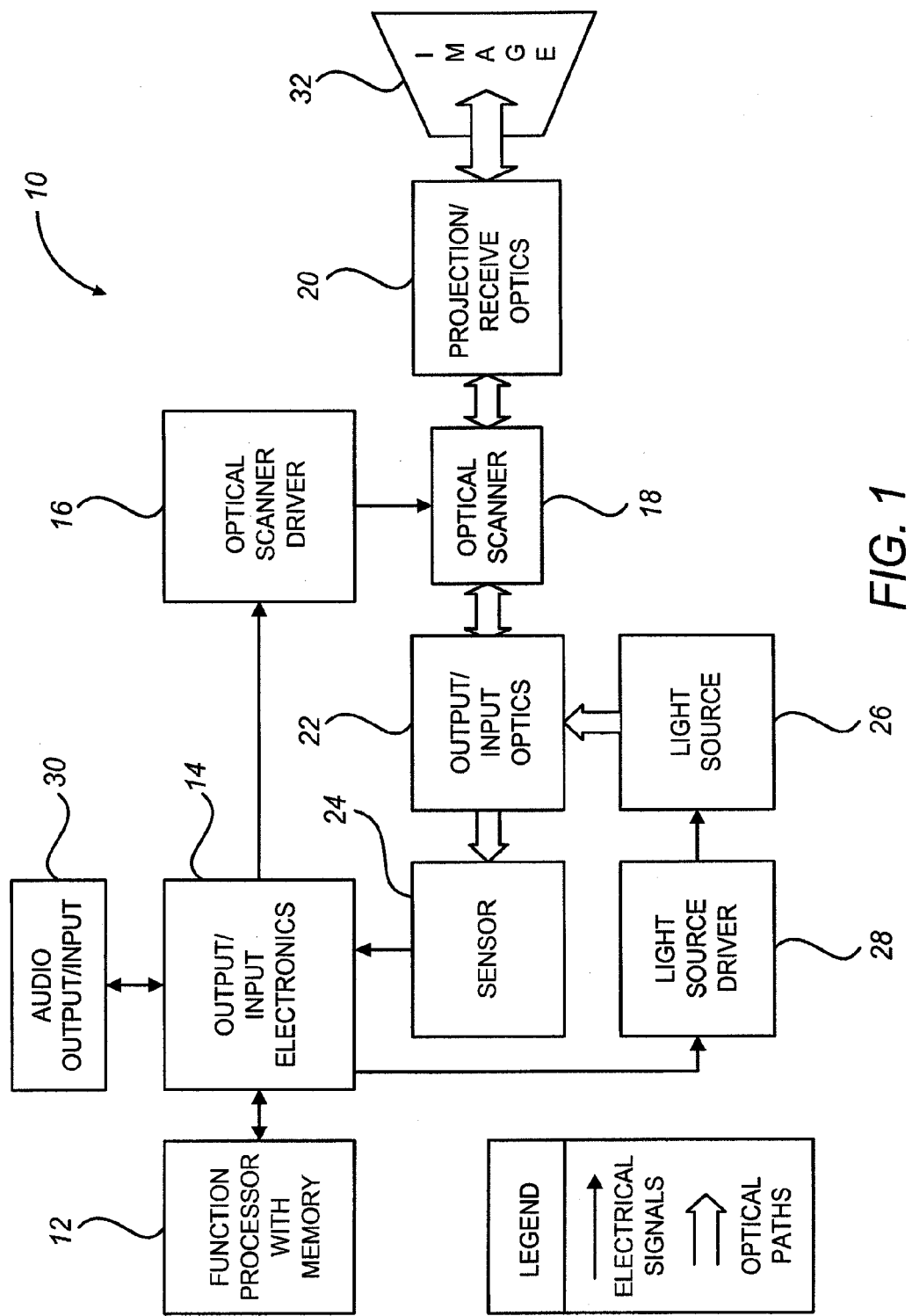
FIG. 1 diagrammatically illustrates a projection and feedback system for projecting an image onto a target area and capturing reflected light from the target area, in accordance with many embodiments.

Improved methods, devices, and systems for projecting an image are provided. In many embodiments, methods, devices and systems for projecting an image and generating feedback via the projected image are provided. Such methods, devices, and systems include an articulated fiber assembly from which a sequence of light is projected to form an image, and in some embodiments, include a sensor for measuring reflections from the projected sequence of light. The ability to measure reflections from the projected sequence of light provides the ability to correlate specific projections and reflections, which, in many embodiments, enables a person to interact with the projected image so as to generate feedback to an electronic device.

Using a high-speed optical scanner and a light source, an image can be projected onto a surface. In many embodiments, the high-speed optical scanner comprises an optical fiber that can be articulated in a scan pattern and light is projected from the articulated fiber to form an image on a target surface. Various light sources can be used. In many embodiments, the light source for such display includes one or more laser light sources. A laser can provide a small diameter beam that is projected from the optical scanner so as to project an image. The small beam diameter can be used to generate a high resolution image. With such a projection device, virtually any surface (e.g., opaque surface) can be used for displaying a projected image. By varying the distance between the projection device and a target surface, the size of the displayed image can be varied. For example, greater distances will increase the displayed image size, whereas smaller distances will decrease the displayed image size. In many embodiments, light source intensity, image size, scanning pattern, and/or scanning parameters are varied and/or modified to achieve desired image characteristics. In many embodiments, the projected image is configured to correctly display on an oblique target surface and/or within a targeted display area. Such variations and/or modifications can be used to achieve desired image characteristics for a variety of target surface characteristics (e.g., size, orientation, reflectivity) and ambient conditions (e.g., illumination).

Various types of optical scanning systems can be utilized in order to provide the desired performance and image generation. Exemplary systems include those having MEMS two axis mirror scanners, as well as optical fiber scanners.

In addition to providing a display, the laser and optical scanner can provide an input function. In use, as the optical scanner scans the beam of light across the display surface, a certain amount of light is reflected back, for example, into the optics of the display generator. This reflected light can be detected and measured. By correlating where the beam is in the displayed image, for example, and the amount of reflected light, certain decisions can be performed. Thus, an image can be displayed and certain interactions (e.g., physical interactions) with the image can be detected. For example, if the image of a keyboard were to be displayed on a surface, and then a finger is placed on a displayed key, the amount of reflected light would change or be detectable, and this would indicate a touched key. Numerous uses and examples are available. Another example would be for a gaming device. Instead of using buttons on the device to interact with the device, the user could use their fingers, hand, body, or other objects for input function.

In addition to the light projected to form a visible image, one or more non-visible wavelengths can also be projected, for example, continuously so as to "illuminate" the target area. Reflections from a non-visible wavelength can be used to track the movement of objects (e.g., a finger as discussed above) that are interacting with the projected image using known methods (e.g., known machine vision techniques). As such, the use of a non-visible wavelength can provide for tracking of an object interacting with the projected image in a way that is less dependent upon the particular image being projected.

Using display and input techniques described herein, very small devices are possible. One such possible device (e.g., gaming device) includes a projection device (e.g., an FSD) built into a shape similar to an ink pen (either a functioning ink pen or a non-functioning ink pen). Other possible devices are handheld electronic devices, such as cell phones, PDAs, laptops, palmtop computers, watches, GPS hand units, and the like.

A projection device (e.g., an FSD) as described herein can have many uses. As further explained, in many embodiments the projection device has substantially simultaneous input and output functions. Since it has substantially simultaneous input and output functions, the projection device can be used for an array of uses. For example, it could be used to read bar codes and then display information about the bar coded item. In another example, it can be used for scanning a printed text or image on a page to be output later by projection, or to another device such as a computer. Such a device configured for reading text and outputting using a built in speaker may be particularly useful, for example, for those that are visually impaired.

FIG. 1 schematically illustrates a projection system 10 for projecting one or more images on a target area and detecting and/or measuring reflected light from the target area, in accordance with many embodiments. The projection system 10 may be used in a wide range of applications, for example, mobile phones, laptops, personal digital assistants (PDAs), MP3 players, smart phones, digital cameras, camcorders, personal mobile televisions, portable projection units, GPS enabled devices, and automobiles. The projection system 10 includes a function processor with memory 12, output/input electronics 14, an optical scanner driver 16, an optical scanner 18, projection/receive optics 20, output/input optics 22, a sensor 24, a light source 26, a light source driver 28, and an audio output/input 30. In many embodiments, one or more of these elements are omitted. For example, in many embodiments, the audio output/input 30 is omitted. In many embodiments, the sensor 24 is omitted, etc.

The function processor 12 includes one or more microprocessors and/or one or more dedicated electronics circuits, which may include a gate array (not shown). The function processor 12 can also include scanner drive electronics, sensor amplifiers and A/D converters (not shown). In many embodiments, the function processor 12 controls actuation of the optical scanner 18 by sending electrical control signals to the optical scanner driver 16. In many embodiments, the function processor 12 also controls activation of the light source 26 by sending electrical control signals to the light source driver 28. Simultaneous actuation of the optical scanner 18 and activation of the light source 26 results in an image 32 being projected for display on a target area. As will be appreciated by those of skill in the art, the methods and techniques of the present invention may be carried out by software modules executed by the function processor 12 and/or by electronic hardware provided in the function processor 12.

In many embodiments, the function processor 12 is in communication with other elements of the projection system 10 via output/input electronics 14. The output/input electronics 14 allows for electrical communication between the function processor 12 and the other elements of the projection system 10 by providing appropriate interfaces as known in the art.

The optical scanner 18 functions to project an image 32 onto a target area via the projection/receive optics 20. In many embodiments, the projection/receive optics 20 include a lens assembly for directing and focusing light directed out of the optical scanner 18 onto the target area. The projection/receive optics 20 may also direct and focus light reflected from the target area to the optical scanner 18 and/or to the sensor 24. Accordingly, the lens assembly in the projection/receive optics 20 may also direct and focus light reflected from the target area onto the optical scanner 18 and/or onto the sensor 24.

The optical scanner driver 16 communicates electrical drive signals to the optical scanner 18 for actuating the optical scanner 18 according to an electrical control signal received from the function processor 12. In many embodiments, the drive signals include two drive signals for actuating a cantilevered optical fiber in a scan pattern about two separate axes.

The light source 26 can be any light source used for projecting the image 32. For example, in many embodiments, the light source 26 is one or more lasers, for example, a red laser, a green laser, and a blue laser, the output of which can be combined as required to produce various image colors. The light source 26 can emit a continuous stream of light, modulated light, or a stream of light pulses. The light source 26 can comprise a plurality of different light sources. For example, the plurality of different light sources can include one or more of a red light source, blue light source, green light source (collectively referred to herein as an "RGB light source"), an infrared (IR) light source, an ultraviolet (UV) light source, and/or a high-intensity laser source. The light sources can be configured to be switchable between a first mode (e.g., continuous stream) and a second mode (e.g., stream of light pulses). If a plurality of light sources are used, a combiner can be used as described below.

In many embodiments, the light source driver 28 communicates electrical control signals to the light source 26 for activating the one or more light sources constituting the light source 26 according to an electrical control signal received from the function processor 12.

The projection system 10 can optionally include output/input optics 22 for communicating light from the light source 26 to the optical scanner 18 and/or for communicating reflected light to the sensor 24. The output/input optics 22 can be a lens assembly, waveguide, or other means for communicating light as is known in the art.

The projection system 10 can optionally include a sensor 24, for example a photo sensor or other known sensor, for detecting light reflected from the target area. The sensor 24 detects, and optionally measures, light reflected from the target area. The sensor 24 can include one or more photo diodes and the like as is known in the art. In many embodiments, the sensor 24 converts the reflected light into an electrical feedback signal and communicates the electrical feedback signal to the function processor 12 via the output/input electronics 14.

In many embodiments, the sensor 24 does not receive light communicated via the output/input optics 22. Rather, the sensor 24 may be placed anywhere where it can detect, and optionally measure, light reflected from the image projected on the target area, for example, closer to the image 32. For example, in many embodiments, the sensor 24 is located adjacent the optical scanner 18 so as to receive reflected light communicated only through the projection/receive optics 20. In many embodiments, the sensor 24 is located adjacent the optical scanner 18 so as to directly receive reflected light.

In many embodiments, the projection system 10 includes an audio output/input 30. The audio output/input 30 can include a speaker, an earphone, a microphone, and the like.

The function processor 12 can be coupled together with a memory. In many embodiments, the memory is separate from the function processor 12. The memory can be used for storing software modules, look-up tables, and algorithms that control the operation and any calibration of the projection system 10. In many embodiments, a control routine is used by the function processor 12 to control the optical scanner 18 and light source 26. The control routine can be configurable so as to match operating parameters of the optical scanner 18 (e.g., resonant frequency, voltage limits, zoom capability, color capability, etc.). The memory can also be used for storing images to be displayed by the projection system 10. As noted below, the memory may also be used for storing data concerning reflections from the target area, threshold values for each pixel of the stored images, parameters of the optical scanner 18, etc.

For ease of reference, other conventional elements that can be included in the projection system 10 are not shown. For example, many embodiments of the projection system 10 of the present invention will typically include conventional elements such as amplifiers, D/A converters and A/D converters, clocks, waveform generators, and the like.

In many embodiments, a projection device can include technology developed for a scanning fiber endoscope (SFE) as described in numerous commonly owned U.S. patent applications and patents, which, for example, include: U.S. Pat. No. 7,298,938, entitled "Configuration Memory for a Scanning Beam Device", filed on Oct. 1, 2004; U.S. patent application Ser. No. 10/956,241, entitled "Remapping Methods to Reduce Distortions in Images," filed on Oct. 1, 2004; U.S. Pat. No. 7,159,782, entitled "Methods of Driving a Scanning Beam Device to Achieve High Frame Rates," filed on Dec. 23, 2004; U.S. patent application Ser. No. 11/969,141, entitled "Methods of Driving a Scanning Beam Device to Achieve High Frame Rates," filed on Jan. 3, 2008; U.S. Pat. No. 7,189,961, entitled "Scanning Beam Device with Detector Assembly," filed on Feb. 23, 2005; U.S. patent application Ser. No. 11/094,017, entitled "Methods and Systems for Creating Sequential Color Images," filed on Mar. 29, 2005; U.S. Pat. No. 7,312,879, entitled "Distance Determination in a Scanned Beam Image Capture Device," filed on Aug. 23, 2005; U.S. Pat. No. 7,395,967, entitled "Methods and Systems for Counterbalancing a Scanning Beam Device," filed on Jul. 21, 2005; and U.S. patent application Ser. No. 12/040,249, entitled "Piezoelectric Substrate Fabrication and Related Methods," filed on Feb. 29, 2008; the complete disclosures of which are incorporated herein by reference. In many embodiments, a SFE, e.g., as described in the referenced publications, can be modified for use as projection device or a display, which can be referred to as a Fiber Scanned Display (FSD). The FSD has been demonstrated using an SFE probe in which the laser light is modulated such that an image can be displayed on a surface. It uses many of the techniques, such as remapping, that are used in the SFE. There are a number of implementation issues that are specific to the FSD. These issues and the unique inventive aspects to address these issues are described herein.

One issue is that the fiber and hence the projected spot may move at different speeds during the specific scan pattern used. For example, when a spiral scan pattern is employed, the projected spot may move slower in the center of the spiral scan and increase in speed as the scan moves outward. In some instances, this can create an image that is bright in the center and darker as it moves outward. In many embodiments, the brightness of the projected light is increased as the scan moves outward thereby providing an improved image for display. The increase can be selected to be proportional to the speed of the spot. This can include changing display timing or signal multiplexing.

It should be appreciated that a wide variety of scan patterns can be employed, for example, a spiral scan pattern, an expanding ellipse pattern, or a Lissajous pattern. The particular scan pattern used can be selected to provide desired image characteristics, for example, resolution, time-dependent surface coverage, intensity, etc.

Another issue addressed is that video is normally generated in a raster pattern which does not fit many of the scan patterns that can be used in an FSD. In many embodiments, an incoming frame of video is stored in a memory buffer and read out of the buffer in the desired manner, for example, according to the scan pattern used. This can include introducing a time delay, such as a one frame time delay (though, could be slightly less) but will not be a problem for typical video. The video buffer can be double buffered. In many embodiments, for example, a projection system includes a buffering means that includes two pieces of memory, where the system would write into a first memory, and output from a second memory.

Another issue addressed is that the frame rate may not match the scanner frame rate as each scanner has a different resonant frequency. In many embodiments, a projection device/FSD can be configured to adjust the number of settling cycles dynamically to match the video frame rate.

Figure 2:
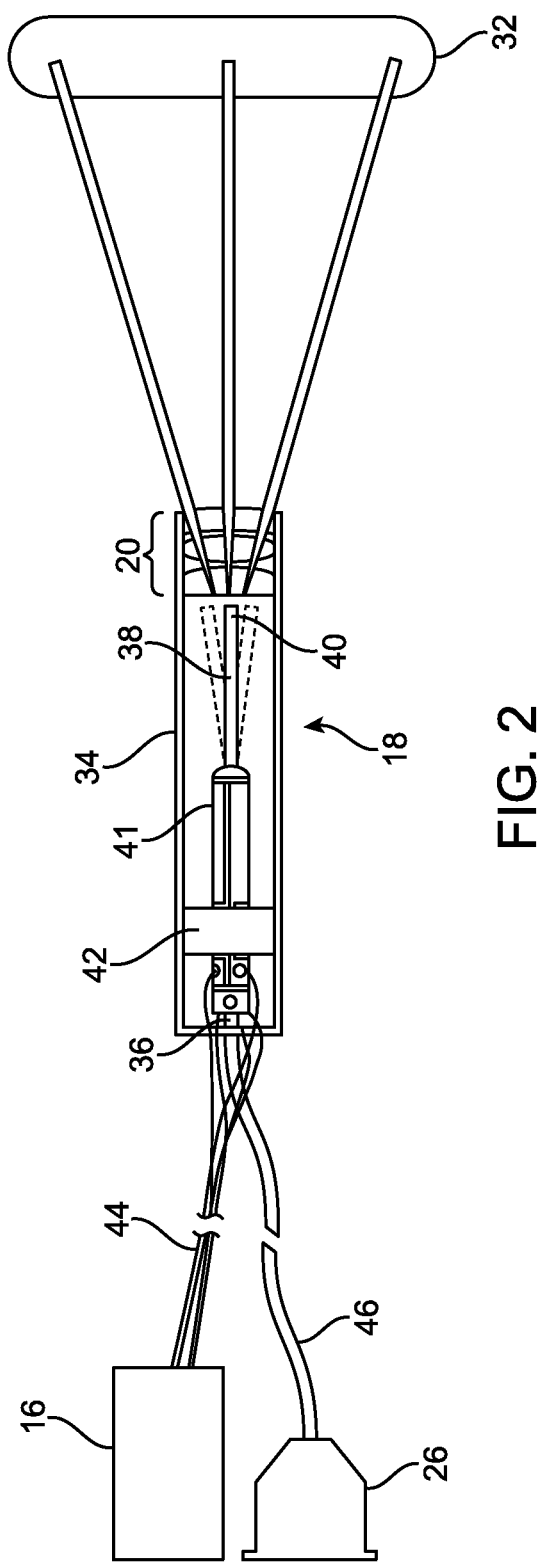
FIG. 2 diagrammatically illustrates a projection assembly that includes an articulated optical fiber for projecting an image onto a target area, in accordance with many embodiments.

FIG. 2 illustrates a projection assembly that can be used in a projection system, in accordance with many embodiments. In this projection assembly, the optical scanner 18 includes an optical fiber mounted within a housing 34. As shown, the optical fiber comprises a proximal portion 36 and a cantilevered distal portion 38 that comprises a distal tip 40. The optical fiber is fixed along at least one point of the optical fiber so as to be cantilevered such that the distal portion 38 is free to be deflected. In many embodiments, the optical scanner 18 includes one or more cantilevered optical fibers. In many embodiments, the optical scanner 18 includes other means by which to project light in a scan pattern, for example, deflectable mirrors, a micro-electomechanical system (MEMS), a galvanometer, a polygon, multiple optical elements moved relative to each other, or the like. While the remaining discussion focuses on scanning fiber devices that are used for displaying images on a target site and, in many embodiments, receiving feedback concerning the generated images, it will be appreciated that alternate scanning means, for example, the aforementioned devices, can be used instead of a scanning fiber device.

The cantilevered distal portion 38 can have any desired dimensions and cross-sectional profile. For example, the distal portion 38 can have a symmetrical cross-sectional profile or an asymmetrical cross-sectional profile, depending on the desired characteristics of the projection assembly. A distal portion 38 with a round cross-sectional profile will typically have substantially the same resonance characteristics about any two orthogonal axes, while a distal portion 38 with an asymmetric cross-sectional profile (e.g., an ellipse) will typically have different resonant frequencies about the major and minor axes. If desired, the distal portion 38 can be linearly or non-linearly tapered along its length.

To articulate the distal portion 38, the distal portion 38 is coupled to the piezo drive electronics 14, which supply one or more drive signals to a fiber actuator 41. The drive signals supplied by the optical scanner driver 16 cause the fiber actuator 41 to actuate the distal portion 38 in a scan pattern. The scan pattern can be one dimensional or consist of a plurality of dimensions. In many embodiments, the scan pattern is two dimensional. In many embodiments, the distal portion 38 is driven at a frequency that is within a Q-factor of the resonant frequency of the distal portion 38, and preferably at its mechanical or vibratory resonant frequency (or harmonics of the resonant frequency). As can be appreciated, the distal portion 38 does not have to be driven at substantially the resonant frequency. However, if the distal portion 38 is not driven at its resonant frequency, a larger amount of energy is required to provide a desired radial displacement of the distal portion 38. In many embodiments, the fiber actuator 41 is a patterned piezoelectric tube. An electrical drive signal from the optical scanner driver 16 causes the piezoelectric tube to actuate the distal portion 38 in a scan pattern so that light emitted from the distal tip 40 is projected to the target area in a desired pattern. The fiber actuator 41 need not be a patterned piezoelectric tube. Rather, in many embodiments, the fiber actuator 41 includes a permanent magnet, an electromagnet, an electrostatic drive, a sonic drive, an electro-mechanical drive, or the like.

In many embodiments, the housing 34 surrounds the distal portion 38 and the fiber actuator 41. The fiber actuator 41 can be mounted within the housing 34 via one or more collars 42. The housing 34 can also house all or a portion of the projection/receive optics 20. The projection/receive optics can be spaced from the distal end 40 of the distal portion 38 so as to focus light emitted from the distal end 40 to, for example, provide better resolution and/or provide an improved field of view for the projection assembly. One or more of the lenses of the projection/receive optics 20 can be fixed relative to the distal end 40 of the distal portion 38 and/or one or more of the lenses of the projection/receive optics 20 can be movable relative to the housing 34.

Although not illustrated in FIG. 2, in many embodiments the sensor 24 (shown in FIG. 1) is disposed within the housing 34. Exemplary techniques for incorporating a sensor 24 are described in U.S. Pat. No. 7,189,961, the complete disclosure of which was incorporated herein by reference above. In many embodiments, the sensor 24 is located so as to receive reflected light via the optical fiber. In such embodiments, the optical fiber functions to receive light reflected from the target area. A technique for using the optical fiber to receive light reflected from the target area is described in U.S. Pat. No. 7,189,961. In many embodiments, the sensor 24 is located outside the optical path of the optical fiber. For example, the sensor 24 can be located adjacent the optical fiber where it may receive light reflected from the target area. In many embodiments, the sensor 24 is omitted.

In many embodiments, the optical scanner driver 16 includes piezo drive electronics. The piezo drive electronics can include one or more microprocessors and/or one or more dedicated electronics circuits which may include a gate array for driving piezoelectric tubes. The optical scanner driver 16 can be provided inside or outside of the housing 34. When the optical scanner driver 16 is provided outside of the housing 34, wires 44 can be used to couple the optical scanner driver 16 with the fiber actuator 41. Providing the optical scanner driver 16 outside of the housing 34 advantageously increases the configurability of the projection system 10 thus increasing the ability to implement the projection system 10 in various applications.

In many embodiments, the light source 26 includes one or more laser diodes. For example, the light source 26 can be one or more light emitting diodes, which can be used to communicate light through fiber optic cables as is known in the art. The light source 26 can be located inside or outside of the housing 34. When the light source 26 is provided outside of the housing 34, an optical path 46 (e.g., an optical fiber, or optical cable) can be used to couple the light source 26 with the distal portion 38. Locating the light source 26 outside of the housing 34 advantageously increases the configurability of the projection system 10 thus increasing the ability to implement the projection system 10 in various applications.

Figure 3:
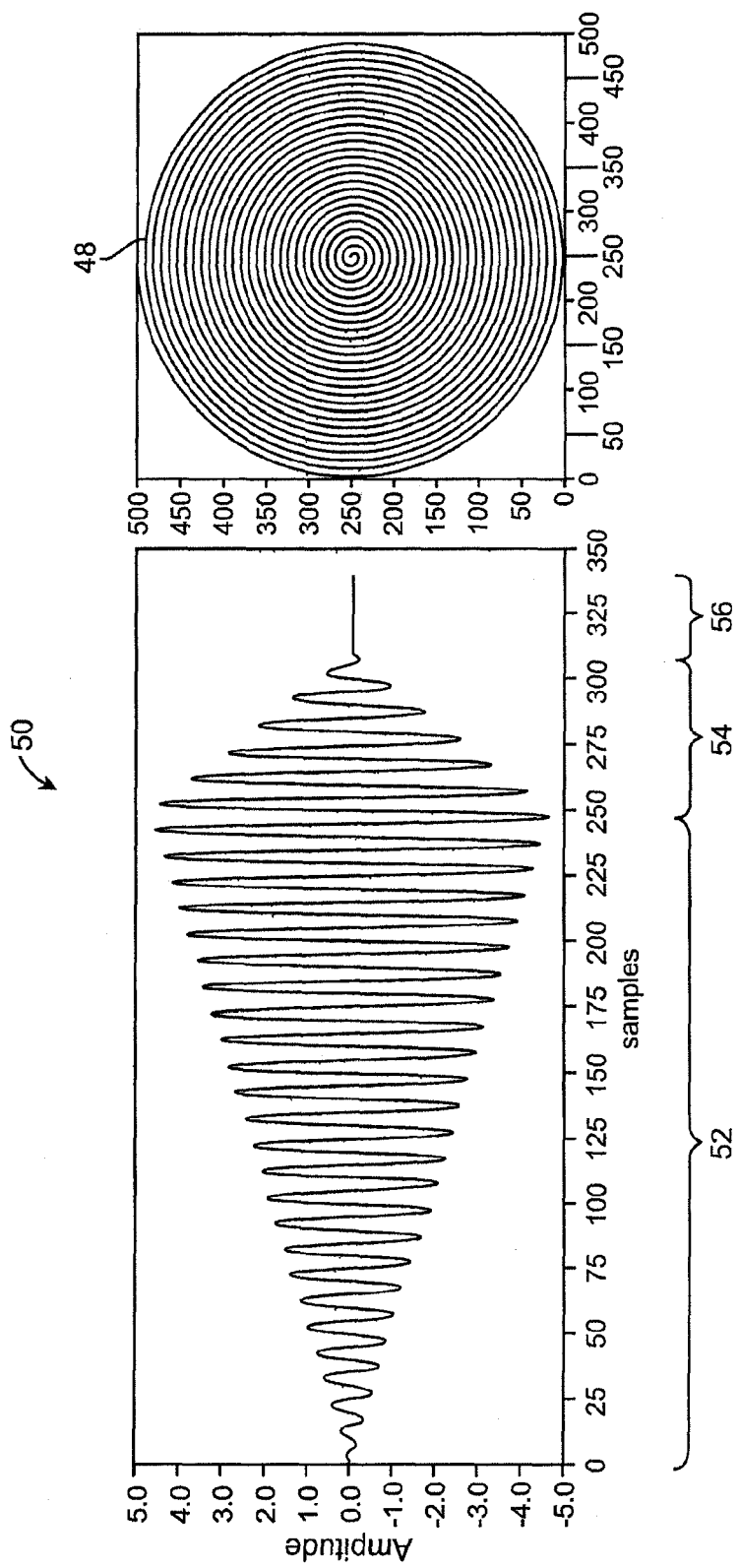
FIG. 3 illustrates a drive signal for articulating an optical fiber used to project an image and a spiral scan pattern of an articulated optical fiber, in accordance with many embodiments.

FIG. 3 illustrates a two dimensional "spiral" scan pattern 48 that can be used in accordance with many embodiments. In many embodiments, the distal portion 38 is actuated to project light in the spiral scan pattern 48 through the use of a horizontal sinusoidal vibration drive signal and a vertical sinusoidal vibration drive signal, both of which have time domain voltage patterns similar to the sinusoidal drive signal 50. The functional processor 12 can be used to control the optical scanner driver 16 such that the optical scanner driver 16 applies these drive signals to the fiber actuator 41. In many embodiments, the sinusoidal drive signal 50 is amplitude modulated in a triangle pattern as shown. In many embodiments, a horizontal and a vertical drive signals are driven with a 90 degree phase shift between them. In many embodiments, such drive signals cause a sequence of light to be projected in a pattern that starts at a central point and spirals outward until a maximum diameter circle is created. The maximum diameter of the circle is a function of the peak amplitude of the sinusoid at the top of the ramp (and the mechanical properties of the cantilevered portion 38).

The sinusoidal drive signal 50 comprises three portions: an imaging portion 52, a retrace portion 54, and a settling portion 56. During the imaging portion 52, the projected sequence of light spirals outward. The imaging portion 52 is typically used for projecting an image 32. During the retrace portion 54, the distal portion 38 spirals inward. In many embodiments, an image is not projected during the retrace portion 54. However, in many embodiments, the retrace portion 54 is used to project an image 32. During the settling portion 56, the distal portion 38 is substantially at rest in the center of the spiral pattern. Therefore, in many embodiments, no image is projected during the settling portion 56. However, the settling portion 56 can optionally be used to project an illumination spot in the center of the spiral pattern.

As can be appreciated, back scattered light (e.g., light reflected from a target area) can be detected at any time projected light is reflected. In other words, back scattered light can be detected during the imaging portion 52, the retrace portion 54, and/or the settling portion 56. As can be further appreciated, the spiral scan pattern is merely one example of a scan pattern and other scan patterns, such as an expanding ellipse pattern, a Lissajous pattern, a rotating propeller scan pattern, a raster scan pattern, a line pattern, and the like, can be used to project a sequence of light onto a target area so as to form an image.

Figure 4:
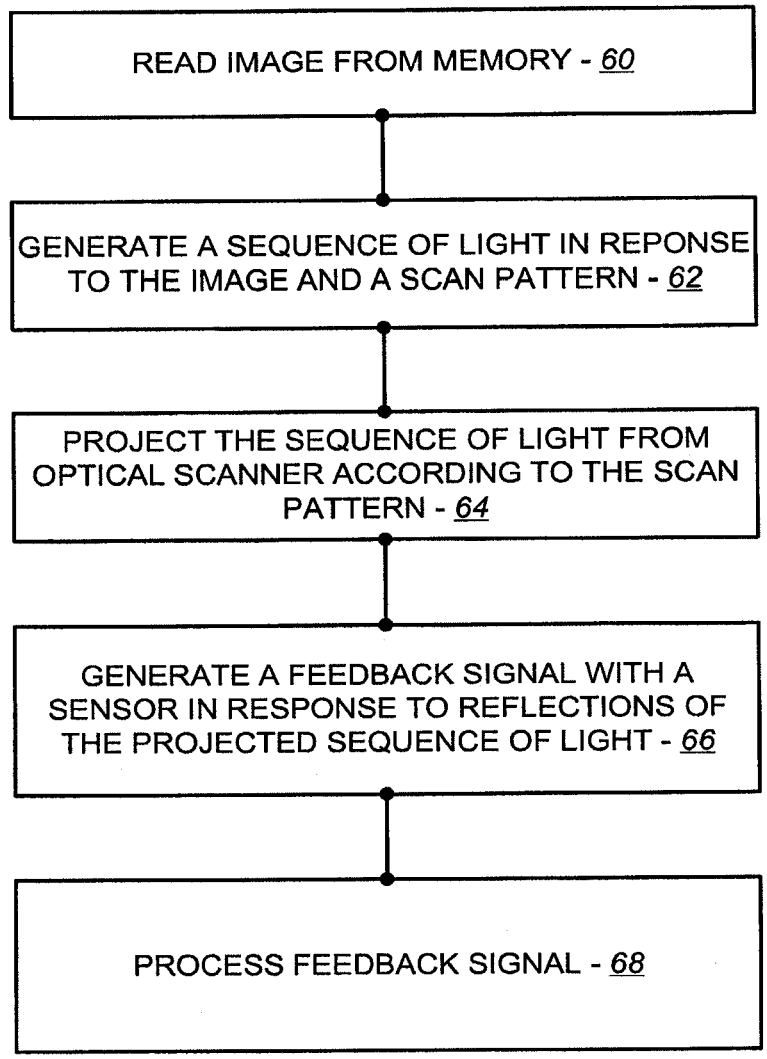
FIG. 4 is a simplified block diagram illustrating a method for projecting an image onto a target area while simultaneously receiving feedback related to the projected image, in accordance with many embodiments.

FIG. 4 is a simplified block diagram illustrating a method for projecting an image on a target area while simultaneously receiving feedback related to the projected images. In use, as the optical scanner 18 projects a sequence of light in a scan pattern towards a target area on a display surface, a certain amount of light is reflected from the target area. This reflected light can be detected and measured. By correlating where the projected light is in the scan pattern with the reflected light detected/measured, information relating to the image and any interactions with the image can be determined. For example, an image can be displayed and certain interactions (e.g., physical interactions) with the image can be detected. For example, if the image of a keyboard were to be displayed on a surface, and then a finger is placed on a displayed key, the amount of reflected light would change or be detectable, which can be used to indicate a touched key. A wide variety of uses are possible. As a further example, such an approach can be used to provide a user the ability to interact with a gaming device by interacting with a projected image using their fingers, hand, body, or other objects instead of physical input features on the gaming device.

In step 60, an image is read from memory. For example, the function processor 12 can be used to read an image from memory. The image can be a single image, or one of a series of images within a sequence of images forming a video.

In step 62, a sequence of light is generated in response to the image and a scan pattern. For example, in many embodiments, the function processor 12 can process the image read from memory on a pixel-by-pixel basis. Each of the pixels in the image read from memory can be processed to generate a resulting sequence of light to be projected via the scan pattern. Depending upon the resolution of the image read from memory and the resulting resolution of the image projected, any particular portion of the generated sequence of light can be a function of one or more of the pixels of the image read from memory.

In step 64, the sequence of light is projected from an optical scanner according to the scan pattern. For example, in many embodiments, the function processor 12 controls the light source 26 via the light source driver 28 to output the sequence of light to the optical scanner in coordination with the scan pattern of the optical scanner. In many embodiments, the light sequence is output from the light source 26 synchronously with the drive signal used to actuate the optical scanner. In many embodiments, the light source 26 emits a single color of light so as to project a monochrome image. In many embodiments, the light source 26 emits various combinations of red, green, and blue light so as to output a color image. As a result, an image can be formed on a target area to which the optical scanner 18 is directed.

In step 66, a sensor is used to generate a feedback signal in response to reflections of the projected sequence of light. For example, for one or more locations of the image formed, reflections from the target area can be detected at practically the same time as the portion of the light sequence projected onto the location is projected. In many embodiments, the reflections can be processed to determine wavelengths and/ or intensities of light reflected from the one or more locations. Information concerning the detected/measured reflections, such as wavelength and/or intensity information, can be stored in memory coupled to or separate from the function processor 12.

In step 68, the feedback signal is processed. For example, for one or more locations of the image formed, the function processor 12 can process the feedback signal to determine whether a user interaction exists. In many embodiments, the function processor 12 determines whether a user or object has interacted image by processing both the portion of the projected sequence of light corresponding to the reflection and the measured reflection. In many embodiments, a non-visible wavelength of light can be continuously projected so as to "illuminate" the target area so that reflections of the non-visible wavelength can be used to track user interactions relative to the image, for example, using known machine vision approaches. Such detected user interactions with the projected image can be used for a wide variety of purposes as will be appreciated by one of skill in the art, and a wide variety of actions can be taken upon detecting a user interaction, including, for example, user notification.

In many embodiments, the feedback signal can be processed so as to avoid nuisance indications of user interaction with the projected image. For example, if a user interaction is indicated via the reflections measured for only a single location, this may be seen as an insufficient basis on which to determine the existence of a user interaction with the projected image. Instead, a user interaction determination can be based on a plurality of reflections from a corresponding plurality of locations. As can be further appreciated, a user need not be notified at all when a threshold value is exceeded. Rather, the function processor 12 may internally store such information, set flags, etc., to be used for other processing decisions.

Numerous techniques exist for the function processor 12 to determine if a user interaction exists. Although certain embodiments follow, other approaches are possible as will be recognized by one of skill in the art.

In many embodiments, the function processor 12 determines an expected reflection characteristic of the corresponding portion of the projected sequence of light and compares the expected reflection characteristic with the measured reflected light characteristic. In many embodiments, the characteristic includes one or more of intensity, color, etc. If a difference between the expected reflection characteristic and the measured reflection characteristic does not exceed a predetermined threshold, then the function processor 12 determines that no user interaction exist. On the other hand, if the difference between the expected reflection characteristic and the measured reflection characteristic exceeds the predetermined threshold, then the function processor 12 determines that user interaction exists.

In many embodiments, the function processor 12 determines the characteristic of a plurality of actual reflected images for a particular location. The characteristics can be averaged over time. The function processor 12 then compares a current measured characteristic of the reflection for the particular location with a previous or the average measured characteristic of the reflection for the particular location. If a difference between the currently measured characteristic and the previous or average measured characteristic does not exceed a predetermined threshold, then the function processor 12 determines that no user interaction exists. On the other hand, if the difference between the current measured characteristic and the previous or average measured characteristic does exceed the predetermined threshold, then the function processor 12 determines that a user interaction exists. This approach may be used in addition to or alternatively to the approach described above using expected reflection characteristics.

In many embodiments, a non-visible wavelength is projected so as to "illuminate" the target area. Reflections of the non-visible wavelength can be used to track movements within the targeted area, which can be used to indicate user interactions. Known machine vision approaches can be used to track movements within the targeted area using known approaches. Such non-visible wavelengths can include a variety of wavelengths, for example, one or more infrared wavelengths.

Figure 5:
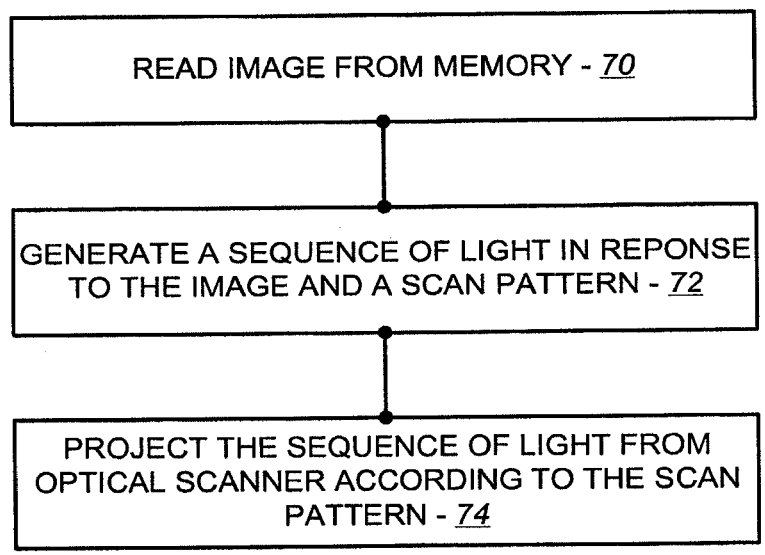
FIG. 5 is a simplified block diagram illustrating a method for projecting an image onto a target area, in accordance with many embodiments.

FIG. 5 illustrates a method of projecting images that can be used in accordance with many embodiments. In step 70, an image is read from memory. For example, in many embodiments, the function processor 12 reads an image from the memory. The image can be a still-image or a single image within a sequence of images for forming a video.

In step 72, a sequence of light is generated in response to the image and a scan pattern. In many embodiments, step 72 can be accomplished similar to step 62 discussed above.

In step 74, the sequence of light is projected from an optical scanner according to the scan pattern. In many embodiments, step 74 can be accomplished similar to step 64 discussed above.

Figure 6:
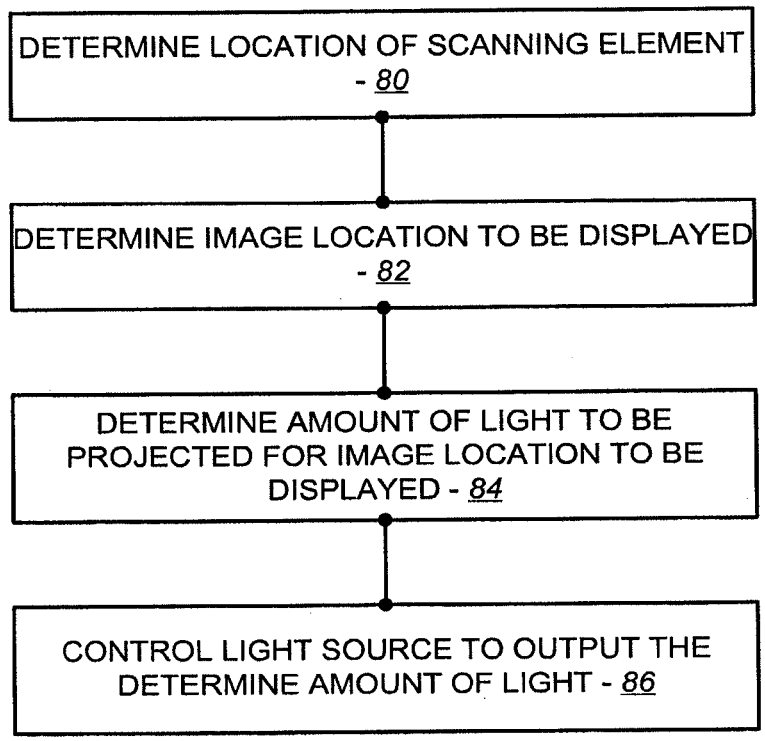
FIG. 6 is a simplified block diagram illustrating a method for controlling the intensity of one or more light sources in a projection system, in accordance with many embodiments.

FIG. 6 illustrates an improvement to step 74, which can be used in accordance with many embodiments. One characteristic of images output from an optical scanner employing a spiral scan pattern is that the image may be brighter in the center of the image and darker towards the outer edges of the image. This characteristic is due to the optical scanner moving at a lower velocity when located closer to the center of the spiral scan compared to a velocity when located further away from the center of the spiral scan. Modifications to the method illustrated in FIG. 5 can improve the quality of the image output from the optical scanner by selectively adjusting the intensity of the sequence of light projected.

In step 80, the location of the scanning element is determined. In many embodiments, as the optical scanner is actuated in patterns such as a spiral pattern, the function processor 12 can determine the location of the optical scanner within the scan pattern. The location of the optical scanner can be determined in a variety of ways. For example, in many embodiments, the function processor 12 determines the location based on the characteristics of the optical scanner and drive signal generated by the optical scanner driver. In many embodiments, a sensor is used to measure the location of the optical scanner. Regardless of the technique used, information relating to the location of the optical scanner can be stored in the memory coupled to or separate from the function processor 12.

In step 82, the image location to be displayed is determined. In many embodiments, the image stored in the memory comprises a plurality of pixels, where each location to be displayed can be a function of one or more of these pixels. The number of pixels involved can depend on the relative resolution of the image stored in memory and the resolution of the location of the image to be formed on account of the scan pattern used.

In step 84, the amount of light to be projected for the image location to be displayed is determined. The amount of light to be projected is a function of the image location to be displayed and the location of the image location within the scan pattern. The location of the image location within the scan pattern impacts the rate at which the light is scanned and, for at least some scan patterns, can impact the relative separation between scanned locations, both of which can impact the amount of light distributed per area at the image location in question. In many embodiments employing a spiral scan pattern, the amount of the light to be projected is increased proportionally to the distance of the location of the optical scanner from a position of rest for the optical scanner. In other words, the amount of light to be projected increases as a distance between a current location of the optical scanner and a center location of the optical scanner increases. In many embodiments, the amount of light to be projected is increased proportional to a velocity of the optical scanner. In other words, the amount of light to be projected increases as a velocity of the optical scanner increases.

The amount of light can be varied by varying the intensity of the light produced by the light source 26 and can be varied by varying the pulse width of the light projected. A combination of an intensity variation and a pulse width variation can also be used. In many embodiments involving a single color light source, the function processor 12 determines the intensity of the light source based on an intensity value of the image location to be displayed. In many embodiments involving multiple light sources that include different color sources, the function processor 12 determines the intensity for each of the light sources. For example, in many embodiments RGB light sources are used. In this case, the function processor 12 determines the intensity of the RGB light sources based on RGB intensity values of the image location to be displayed. Similar approaches can be used when pulse width variation is used, or when a combination of intensity variation and pulse width variation is used.

In step 86, the light source is controlled to output the determined amount of light. Various known methods for varying the amount of light through intensity variation, pulse width variation, or a combination of the two can be used.

Figure 7:
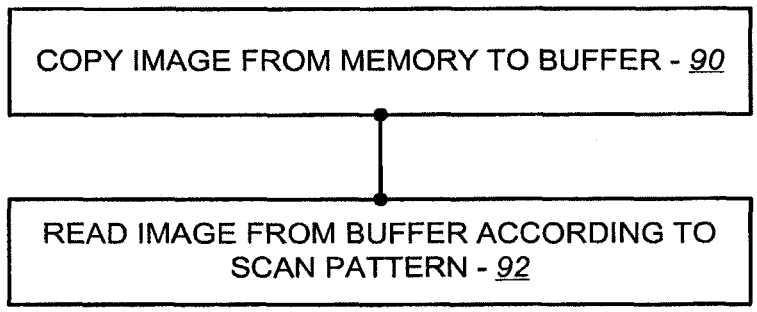
FIG. 7 is a simplified block diagram illustrating a method for writing an image to a buffer and reading the image from the buffer according to a scan pattern, in accordance with many embodiments.

FIG. 7 illustrates an improvement to step 70 in the method of FIG. 5. Video is often generated in a raster pattern. Where the optical scanner is controlled to generate a non-raster scan pattern, for example, a spiral scan pattern, the scan pattern does not match the raster pattern. In many embodiments, a modifications to the method illustrated in FIG. 5 involves copying an image to a buffer and reading the buffered image in accordance with the scan pattern used.

In step 90, the image is copied from memory to a buffer. For example, in many embodiments the function processor 12 copies sequential images from a video stored in the memory to a buffer. The buffer may be coupled to or separate from the function processor 12.

In step 92, the image is read from the buffer according to the scan pattern employed. For example, in many embodiments, the function processor 12 reads the images out of the buffer in a manner appropriate for the scan pattern, for example, a spiral scan pattern. This can include introducing a time delay, such as a one frame time delay (though, the delay can be slightly less). However, such a time delay is not likely to have a detrimental affect on most video. In many embodiments, the buffer is double buffered. In many embodiments, the projection system 10 includes two pieces of memory (either coupled to or separate from the function processor 12), where the projection system 10 would write into a first of the two memories, and output from a second of the two memories.

Figure 8:
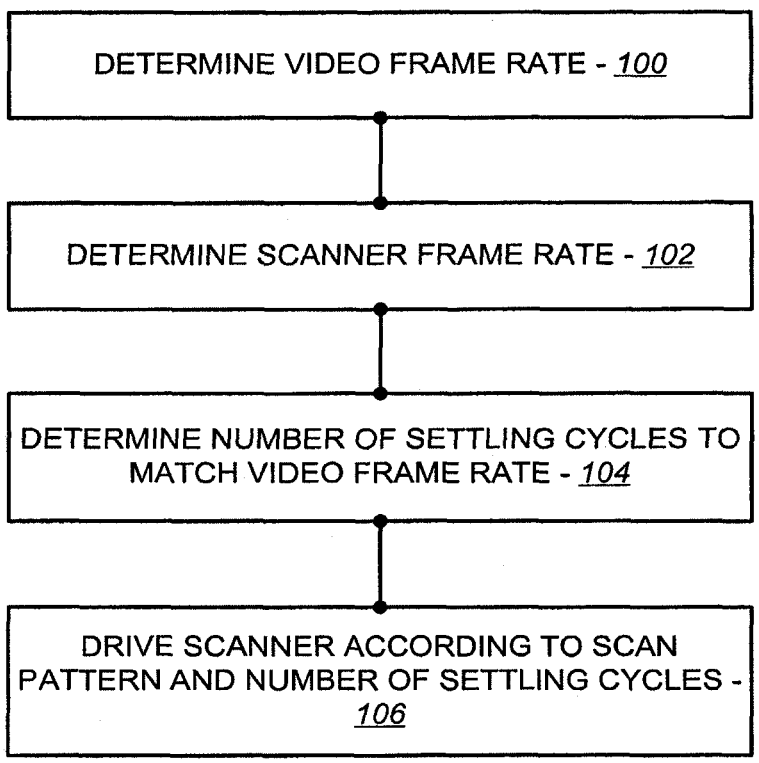
FIG. 8 is a simplified block diagram illustrating a method for matching the frame rate of a projection system to a video frame rate, in accordance with many embodiments.

FIG. 8 illustrates in improvement to step 74 in the method illustrated in FIG. 5. The optical scanner has a frame rate that is dependent upon the characteristics of the optical scanner, such as the resonant frequency of the optical scanner, as well as upon the scan pattern employed. Where the projection system 10 projects a video, the video has a frame rate based on the coding of the video. The frame rate of the optical scanner may not be equal to the frame rate of the video. The steps illustrated in FIG. 8 can be used to match the frame rate of the optical scanner with the video frame rate.

In step 100, the video frame rate is determined. In many embodiments, the function processor 12 determines the frame rate of a video to be projected. For example, the frame rate can be determined by analyzing the properties of the video. Information concerning the frame rate of the video can be stored in the memory coupled to or separate from the function processor.

In step 102, the scanner frame rate is determined. For example, in many embodiments, the frame rate of the optical scanner is pre-stored in the memory. In many embodiments, the function processor calculates the frame rate of the optical scanner based on user-inputted characteristics of the optical scanner. Information concerning the frame rate of the optical scanner can be stored in the memory.

In step 104, the number of settling cycles required to match the video frame rate are determined. In many embodiments, the function processor determines the number of setting cycles necessary to match the frame rate of the optical scanner to the frame rate of the video. For example, in many embodiments, the function processor determines the length of the settling portion 56 of the sinusoidal drive signal 50 illustrated in FIG. 3. The number of settling cycles can be increased to effectively decrease the frame rate of the optical scanner. Accordingly, the number of settling cycles can be varied so that the frame rate of the optical scanner is equal to the frame rate of the video.

In step 106, the scanner is driven according to the scan pattern and the number of settling cycles. In many embodiments, the function processor 12 controls the optical scanner driver 16 to drive the optical scanner 18 according to the scan pattern and the number of settling cycles.

Figure 9:
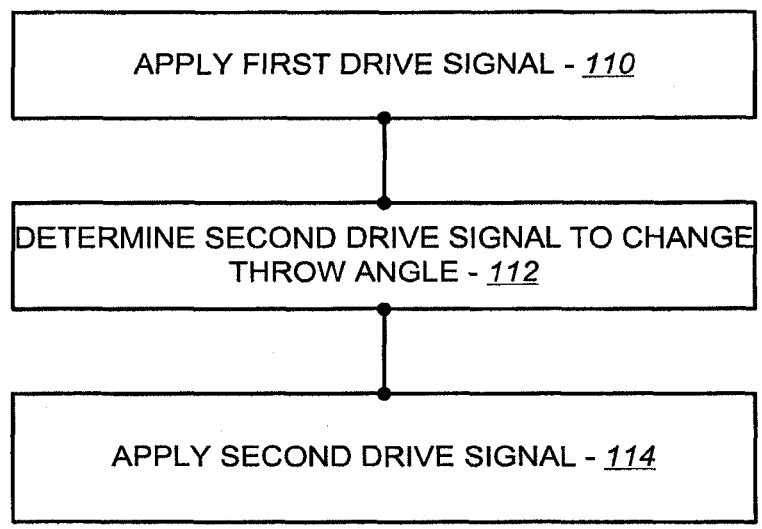
FIG. 9 is a simplified block diagram illustrating a method for changing the field-of-view of a projection system, in accordance with many embodiments.

FIG. 9 illustrates in improvement to the method illustrated in FIG. 5. The projection system 10 projects an image having a size that corresponds to a maximum voltage of the electrical control signal used to drive the optical scanner 18. For example, as illustrated in FIG. 3, the outer diameter of the spiral scan pattern 48—and thus a size of a projected image for a given distance—is based in part on the maximum voltage of the sinusoidal drive signal 50. Thus, variation in the drive signal can be used to adjust the scan angle. Such a variation can be employed in a variety of ways, for example, as desired by the user or dynamically on a frame-by-frame basis. This technique may be used to create a desired image size at varying projection distances. For instance, a user browsing the internet at a desk placed against a wall may use a wider scan angle to produce a large image at a relatively short throw distance, and a narrower scan angle to project a presentation on a distant wall at a meeting. In many embodiments, throw angles ranging from 30 degrees to 100 degrees can be used.

In step 110, a first drive signal is applied to the optical scanner thereby resulting in a first throw angle. In step 112, a second drive signal can be determined that will change the throw angle. In step 114, the second drive signal is applied to the optical scanner thereby resulting in a change in throw angle from the first throw angle. For example, during a single frame employing a spiral scan pattern, the rate of increase of the scan angle can be increased as the scan pattern moves from the center portion of the scan pattern and outward.

In many embodiments, a resolution of the projected image can be traded off with the frame rate of the projected image. In other words, resolution of the projected image can be increased at the cost of a decreased frame rate. Similarly, the frame rate of the projected image can be increased at the cost of a decreased resolution of the projected image. In many embodiments, the same optical scanner is used to generate 240-line images at 60 Hz, 600-line images at 30 Hz, and 1000-line images at 15 Hz. The tradeoff occurs because the more dense scan patterns required to produce an increased resolution image take longer to complete as compared to the less dense scan patterns used to produce lower resolution images. For example, with a spiral scan pattern, more spirals are needed for a higher resolution image, and the additional spirals take additional time to complete. Advantageously, higher resolutions can be used when projecting still images whereas higher frame rates can be used when projecting video.

Figure 10:
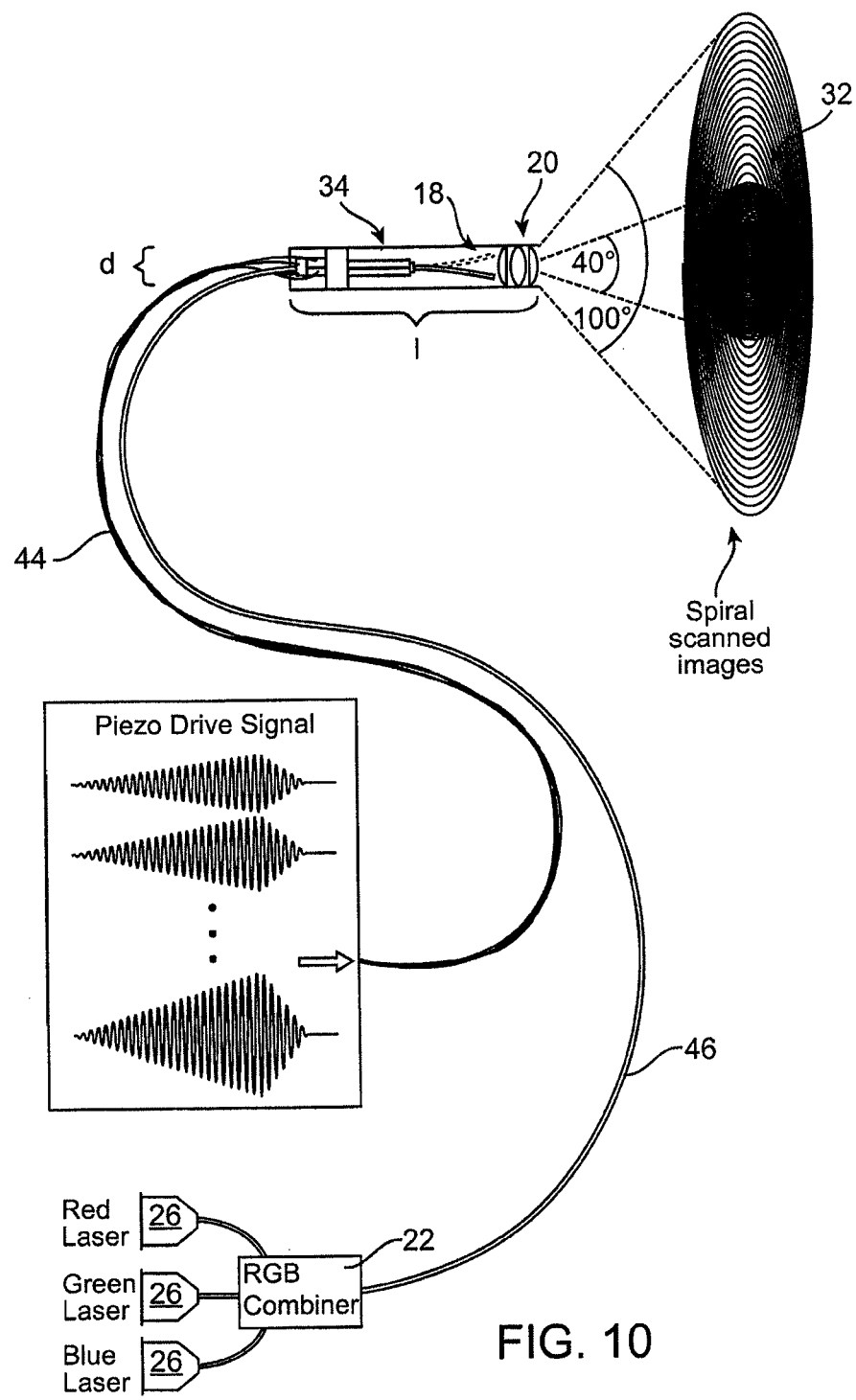
FIG. 10 diagrammatically illustrates an articulated fiber projection system that can project a sequence of light output from red, green and blue lasers, in accordance with many embodiments.

FIG. 10 illustrates a projection assembly in accordance with many embodiments. The components of the projecting assembly are identical to those illustrated in FIG. 2 except for as follows. In this projection assembly, the housing 34 has a length (l) equal to approximately 9 mm and a diameter (d) equal to approximately 1 mm. The optical path 46 is a single mode optical fiber, and the optical scanner driver creates and applies sinusoidal drive signals having different maximum amplitudes at different times so as to vary the throw angle as discussed above. The light source 26 consists of a red laser, a green laser, and a blue laser. The output/input optics 22 includes an optical combiner that functions to combine an output from the red laser, green laser, and blue laser and communicate the combined signal to the optical path 46.

Figure 11:
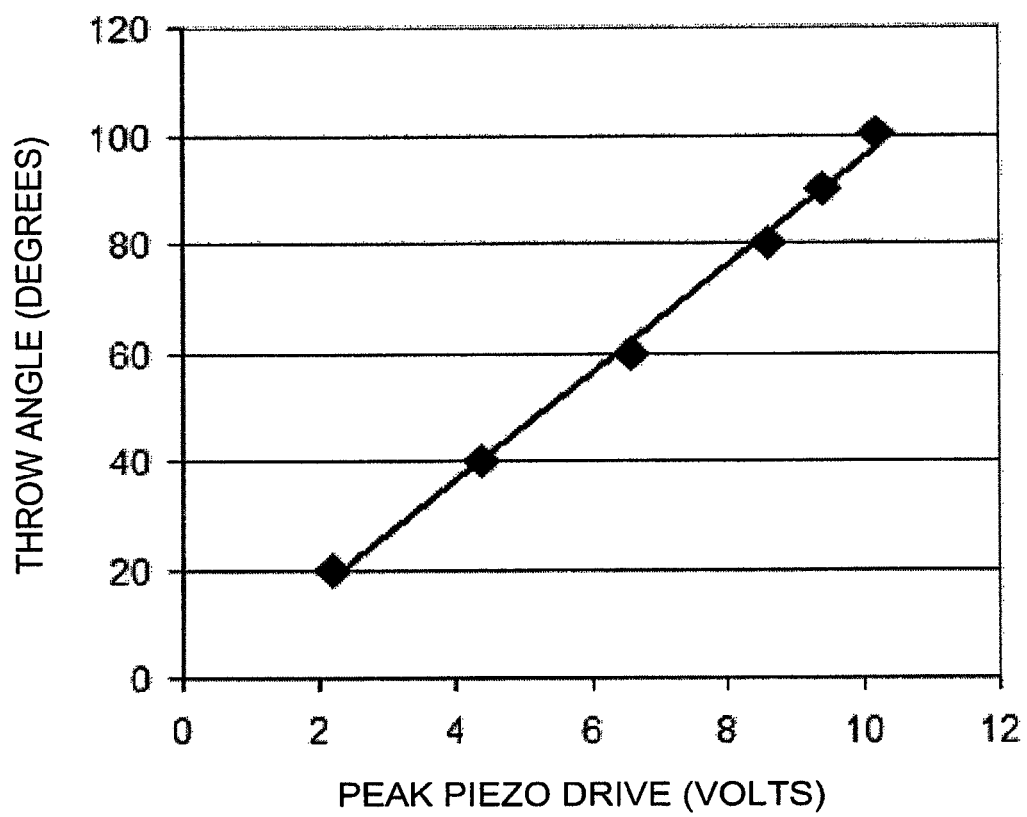
FIG. 11 illustrates a functional relationship between peak drive signal and resulting throw angle for an articulated fiber projection system, in accordance with many embodiments.

FIG. 11 illustrates the relationship between peak drive voltage and projector throw angle for an example optical scanner comprising a scanning cantilevered fiber. The optical scanner used comprises a single-mode optical fiber, the tip of which has been inserted into a 0.4 mm diameter hollow piezoelectric actuator, as illustrated in FIG. 10. The piezoelectric actuator was vibrated at a constant 11,532 Hz scan rate, producing 500 line spirals with a 30 Hz frame rate. The peak voltage was electronically adjusted and drive voltages that produced 20 degree, 40 degree, 60 degree, 80 degree, 90 degree, and 100 degree throw angles were measured. As can be seen from FIG. 11, the relationship between throw angle and peak drive voltage for the example optical scanner is nearly linear.

Figure 12:
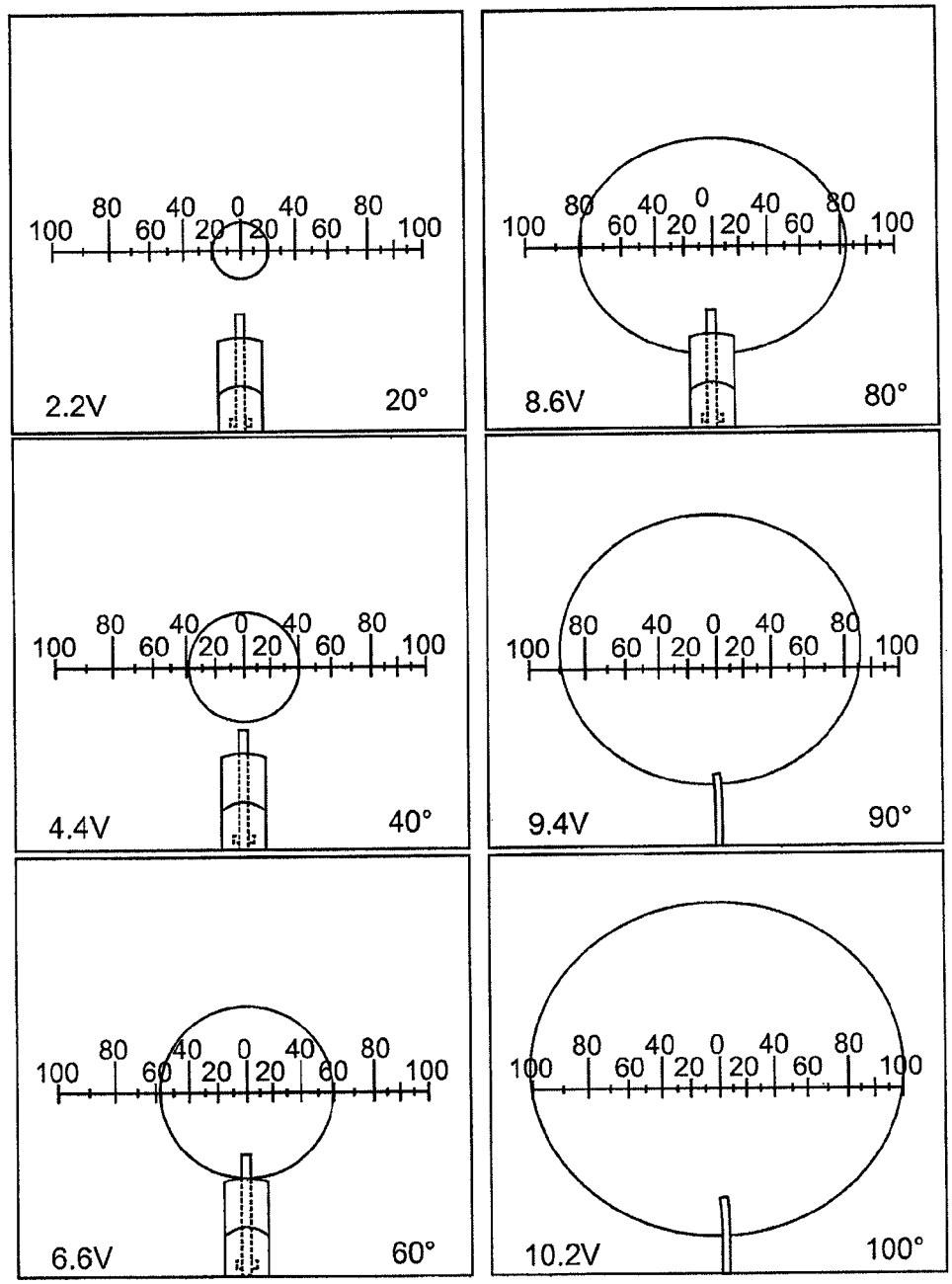
FIG. 12 illustrates the generation of the throw angle data points of FIG. 11.

FIG. 12 contains photographs of each projected spiral for the data of FIG. 11. It is interesting to note that at very wide throw angles, the light is passing through the extreme periphery of the projection lenses, and lateral chromatic aberration becomes apparent as shorter wavelengths (blue) are refracted at sharper angles than longer wavelengths (red). This can be corrected either optically or digitally, by a relative scaling of each color channel. One can also see shadows at the bottom edge of the 100° throw angle spiral caused by bits of adhesive at the edges of the miniature projection lenses.

The ability to vary throw angle can be used to provide a number of significant benefits. For example, it may often be the case that the optimal projected image size will be a function primarily of the ambient lighting conditions and the reflectivity of the surface. For example, for a particular lighting condition, a projected image the size of an 8.5"×11" piece of paper may be the largest projected image size that possesses enough luminance to be usable to the viewer, so that if the viewer moves the projector farther away from the screen (which would normally increase the size of the projected image), it may be useful to automatically reduce the throw angle to keep the image scaled to 8.5"×11" or less. This may be a fairly common scenario, for example, if the projector were incorporated into a laptop computer that is projecting an image onto a wall behind a desk and the user periodically repositions the laptop on the desk for ergonomic typing comfort, etc. The throw angle can also be adjusted, for example, by changing the "mode" of the projection device. For example, when a projection device projects a web browsing window on the surface of a desk from a short distance, the throw angle can be increased to create a large usable image from a short throw. When the device is placed in "movie mode" to project a video on a more distant wall, the throw angle can be reduced to maintain a desired projection size with a usable image brightness. Such a mode change can be accomplished manually via user input, or automatically. For example, the device can be configured such that when the appropriate digital content loads, it automatically switches modes. For example, if the user is browsing the web in a small projected window with a 3 by 4 aspect ratio, and the new web page contains an embedded movie clip, then the device can automatically switch the aspect ratio of the projection to match that of the clip (e.g., 16×9) and/or rescale the total size of the projected window.

Figure 13:
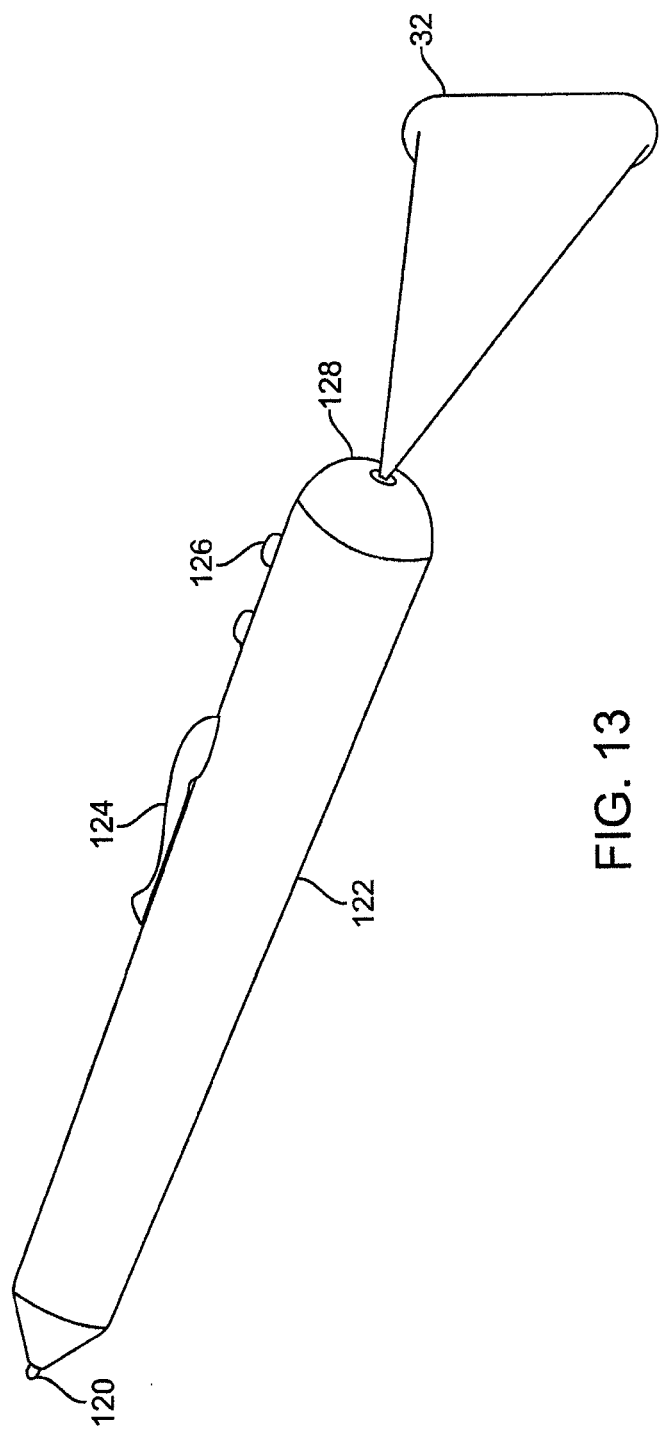
FIG. 13 illustrates a projection system incorporated into a writing instrument, in accordance with many embodiments.

FIG. 13 illustrates a projection system incorporated together with a writing instrument. The writing instrument can be a pen, pencil, or electronic writing tool. The writing instrument can include a writing end 120, a body 122 for encasing the elements of the projection system and additional elements of the writing instrument, such as a clip 124 for removably attaching the writing instrument to objects, a user interface 126 for receiving user inputs so as to allow a user to control the projection system, and a projection end 128 for projecting an image 32. In many embodiments, the elements of the projection system and the projection assemblies illustrated in FIG. 1, FIG. 2, and FIG. 10 can be encased in the body 122.

Figure 14:
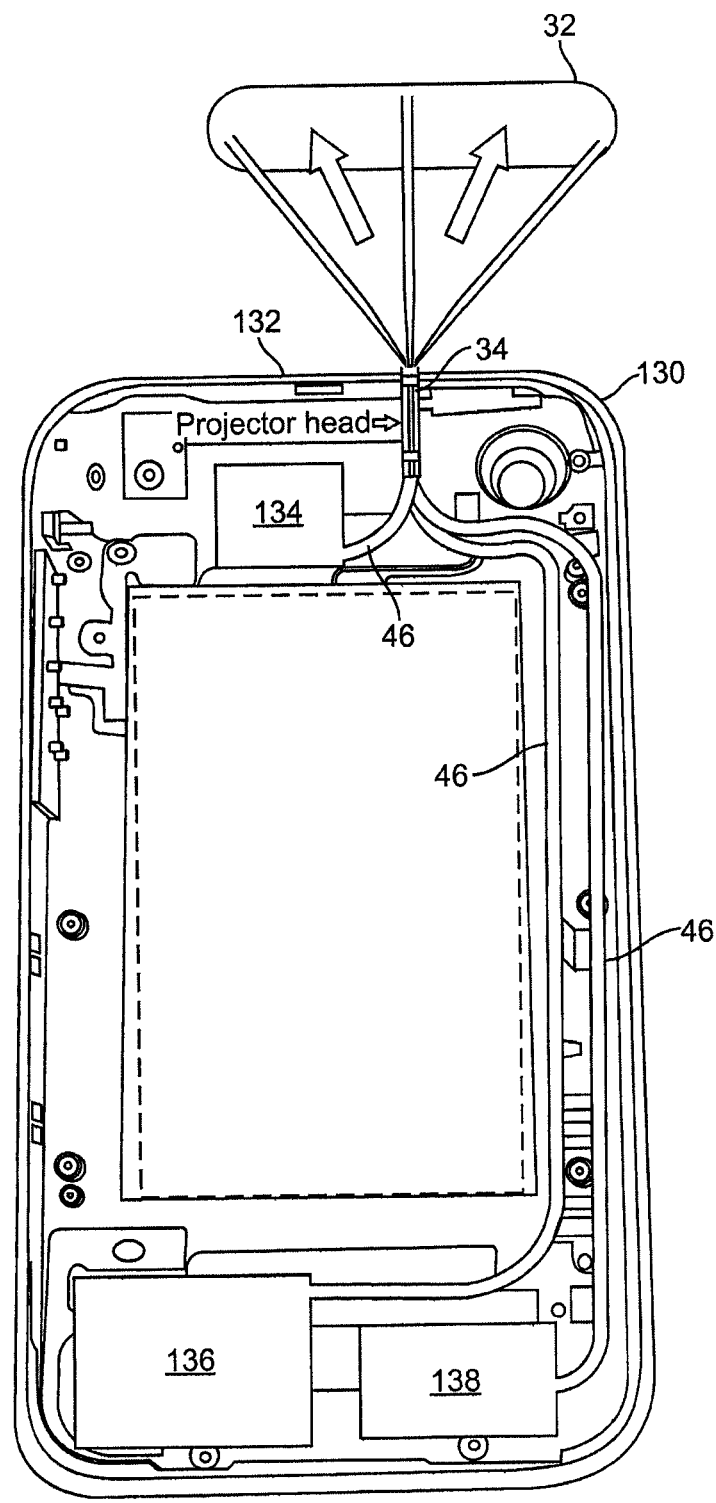
FIG. 14 illustrates a projection system incorporated into a handheld electronic device, in accordance with many embodiments.

FIG. 14 illustrates a projection system in accordance with many embodiments. The elements of this projection system are incorporated together with a handheld electronic device, such as a mobile phone, personal data assistant (PDA), and the like. The handheld electronic device includes a body 130 for encasing the elements of the projection system and elements of the electronic device. The housing 34 of the projection system can be provided at a distal end 132 of the handheld electronic device for projecting the image 32. In many embodiments, the projection system includes a red laser 134, a green laser 136, and a blue laser 138. In many embodiments, use of separate optical paths 46 and an optical coupler adjacent or within the housing 34 advantageously enables flexible placement of the red laser 134, green laser 136, and blue laser 138 so to achieve efficient implementation of the projection system.

Additional Projected Content and/or Feedback Features

In many embodiments, a non-rectangular scan pattern (e.g., a spiral scan pattern, an expanding ellipse scan pattern) are used to project available images having a rectangular format (e.g., video clips). The display of rectangularly-formatted content in a non-rectangular projection area can be executed in a number of different ways, with various advantages. For example, the rectangular content can be cropped to match the shape of the projection area, such that the entire scan is filled with the rectangular format content. Additionally, the cropping can be dynamically adjusted to show different portions of the image over time (e.g., if a circular projection is used to project a slide show of rectangular photographs, the circular "window" can pan or scan across the total rectangular image over time).

Figure 15A:
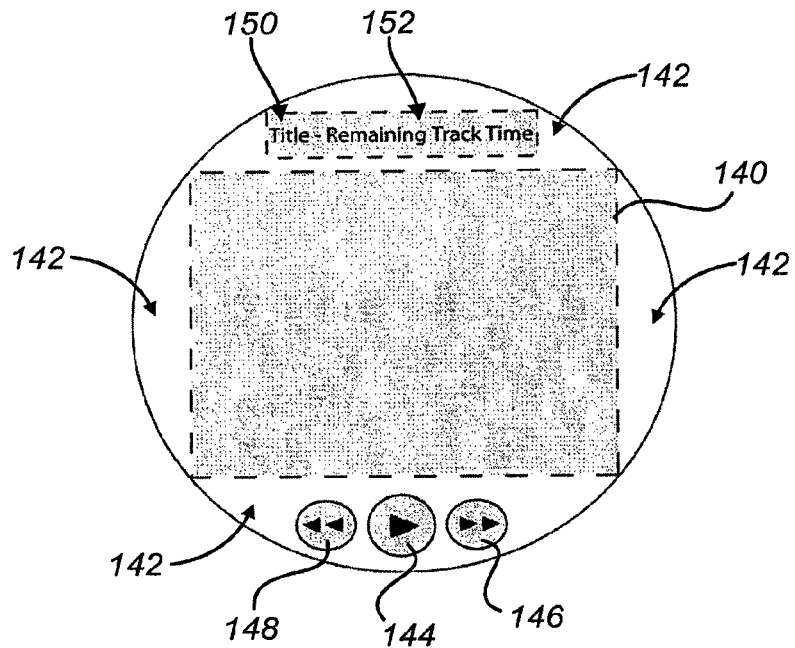
FIG. 15A illustrates the use of fringe areas of a projection area to display additional image content, in accordance with many embodiments.

As an alternative to cropping the content to fit the shape of the projection area, the content can be reduced in size to fit within the non-rectangular projection area. In such a configuration, portions of the total projection area will be unused for the rectangular content. For example, if a rectangular image is scaled to fit within a circular projection area, such that its corners align with the circumference of the circular scan, there will be four portions of the circular projection area (round on one side and flat on the other) that are not being used to display the rectangular content. To make use of this free space, as illustrated in FIG. 15A, the device software can fill this space with additional content, such as context-appropriate information about the primary content or controls for the device. For example, if a rectangular movie clip 140 is being presented within a circular projection area, the four "fringe areas" 142 can display play 144, pause, stop, fast forward 146, and rewind buttons 148 for the movie, the title of the movie 150, the time elapsed or time remaining in the clip 152, etc. As another example, if a rectangular webpage is viewed in a circular projection area, the fringe areas can display the URL of the webpage; back, forward, history, bookmarks, etc., buttons, and other information relevant to the webpage. Additionally, these fringe areas can be used to alert the user of information that does not directly pertain to the rectangular content currently being viewed. For example, while a viewer is editing a rectangular spreadsheet in a circular projection area, the fringe areas can be used to alert the user that he/she has received a new email and/or to display the current time and date. The fringe areas can also be used for user input functions that are enabled by the generated feedback signal. For example, the fringe areas can be used for user feedback purposes, with our without the display of any additional content the fringe area. For example, the fringe areas can be made sensitive to "key presses" by the user touching his/her finger to the fringe area or "scrolling" his/her finger across a fringe area, even if "buttons" or "scroll bars" are not rendered in those areas.

Device Orientation Compensation

Figure 15B:
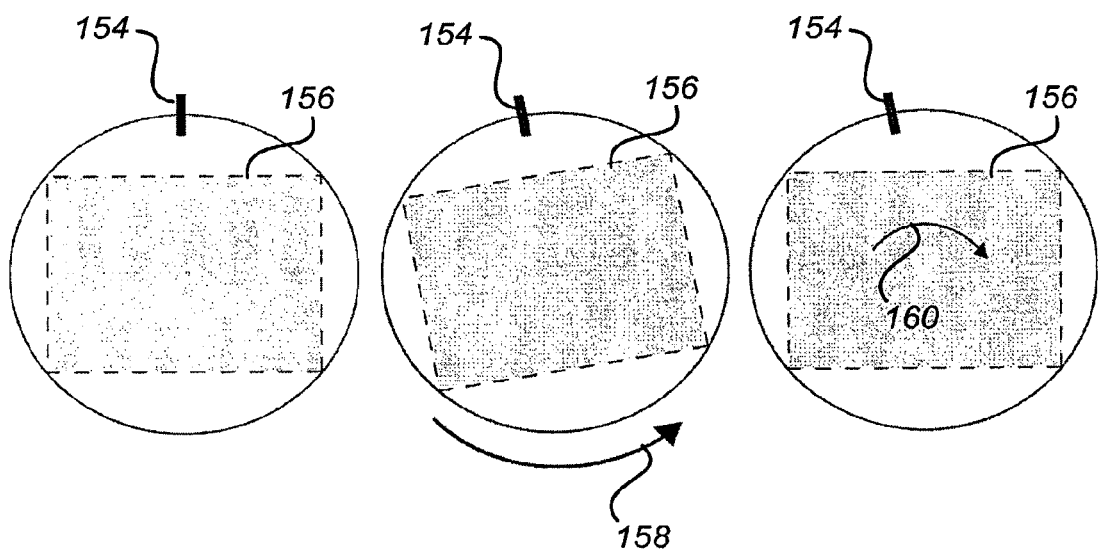
FIG. 15B illustrates the dynamic orientation of a projected image in response to projection device roll, in accordance with many embodiments.

In many embodiments, device orientation compensation is used to dynamically orient and/or position a projected image. A projected image can be dynamically oriented and/or repositioned within a scan pattern in response to a movement of the projection device relative to the projection surface and/or viewer. For example, when the projection device is rolled relative to the projection surface, this movement can be detected and used to reposition the projected image within the projection area, such that the content remains horizontally aligned and stable even when the projection device is rolled and tilted (as illustrated in three sequential time steps shown in FIG. 15B). In the first time step, the projection device is held level, with the marker 154 at the top of the circle signifying the orientation of the projection device. In the second time step, the projection device is rotated ten degrees, and the rectangular sub-image 156 is shown as being displayed at an angle (pre-compensation). The curved arrow 158 illustrates the rotation of the projection device and the projection area. The marker 154 on the circle is to the left of center. In the third time step, the projection device remains rotated at ten degrees, and the rectangular sub-image 156 has been rotated by negative 10 degrees to compensate for the projection device rotation. The small arrow 160 illustrates the rotation of the rectangular sub-image 156. The marker 154 on the circle remains to the left of center because the projection device is still rotated 10 degrees relative to the starting position. Such minor rolls, tilts, tips, and pans can be common especially when the device is hand-held by a user, and it can be very valuable to stabilize the image. Device movements, such a device roll, can be compensated for in a variety of ways. For example, with device roll, compensation can be provided by a simple rotation of the image data in a memory buffer.

Projection device movement can be detected in a variety of ways. For example, the movements of the device can be detected using the feedback function described above. The movements can also be detected using one or more orientation sensors. For example, a tilt sensor or accelerometer can be used to detect a rolling of the device relative to the projection surface, and the projected image can be remapped within the scan pattern to compensate for this rolling and keep the image properly oriented (e.g., level with the horizon). If additional content is displayed in the "fringe areas" as described above, this content can simply be rotated along with the main image, in order to keep the entire displayed image properly oriented.

The following examples are intended to illustrate but not limit the present invention.

EXAMPLES

Prototype light-scanning engines that use a vibrating optical fiber to scan light in two axes were developed. Rather than reflecting light from a scanning element, the light is deflected directly as it emerges from being transmitted along the optical fiber, enabling a reduction in total scanner size. Initial prototypes were used to develop wearable displays for users with low vision; however, a raster-scanning approach using two orthogonal piezoelectric actuators limited display resolution to 100×39 pixels. Subsequent development focused on using scanning fiber engines to create ultra-thin endoscopes and dramatic improvements to the core fiber-scanning technology have been achieved.

A proof-of-concept compact monochrome scanned-laser projection display prototype using an improved scanning fiber engine capable of producing 500 line by 500 pixel images with a maximum throw angle of 100° was developed. The scanner is dynamically configurable; the scan angle can be adjusted dynamically to accommodate different screen sizes at variable projection distances, and resolution can be traded for frame rate to optimize for high resolution still images or high frame rate video presentation.

The miniature projector vibrates the tip of a fiber optic in two axes to spirally-scan a spot of light that is luminance-modulated to form a projected image. The scanned light is nearly collimated, enabling clear images to be projected upon both near and distant surfaces. The total size of the scan engine, including lenses and outer housing, is 1.07 mm (diameter) by 13 mm (length).

At the heart of the scanning engine is a fused silica optical fiber that has been inserted through a hollow piezoelectric actuator (PZT 5A material), such that a short length of fiber protrudes from the tip of the actuator to form a flexible cantilever (see, e.g., FIG. 2). The piezoelectric actuator vibrates the fiber cantilever at its first mode of mechanical resonance. This mechanical resonance amplifies a small vibration at the tip of the actuator by several hundred times to vibrate the tip of the optical fiber through a large scan angle (producing a final throw angle of up to 100° after the lens system), and smaller scan angles can be produced with lower drive voltages to the piezoelectric actuator.

Quadrant electrodes, plated on the 0.4 mm diameter piezoelectric tube, enable the driving of two orthogonal axes of motion at the fiber tip. An amplified sine wave to one axis and a cosine wave to the other axis of the actuator generate a circular scan. Modulating the amplitudes of the drive signals creates an area-filling two-dimensional spiral scan pattern (see, e.g., the right side of FIG. 3).

The optical fiber has a 125 μm cladding diameter and a cantilever length of 4.3 mm, producing a first-mode resonance of approximately 5 kHz. The actuator is driven at or near this resonance frequency with one axis 90 degrees out of phase with the other to form a circular scan. A spiral scan of 250 rings is generated by increasing the voltage linearly to a maximum voltage defining the maximum scan angle for that frame. The fiber is driven back to zero during the retrace portion of the triangular shaped, amplitude-modulated sine wave, as illustrated in, e.g., FIG. 3. A short settling time is used between individual frames of scanning at fiber resonance.

The scan angle of the scanning fiber projection display can be adjusted by varying the maximum drive voltage to the piezoelectric actuator. For very short throw distances, e.g., for shallow rear-projection displays, a maximum drive voltage can be used to produce a throw angle of up to 100°. For front projection from a mobile device, a more modest throw angle (e.g., 30°) may be produced by using a lower drive voltage. Additionally, this scan angle may be adjusted dynamically by the device to create a desired image size at varying projection distances. For instance, a user browsing the internet at a desk placed against a wall may use a wider scan angle to produce a large image at a relatively short throw distance, and a narrower scan angle to project a presentation on a distant wall at a meeting.

For this initial proof-of-concept demonstration, a luminance-modulatable diode laser (Melles Griot, model 57 ICS 072/S) was coupled to the base of the single-mode optical fiber to project red light from the fiber cantilever tip. Pixel-modulated light was projected through the fiber for 50 ms each frame, with an additional 83 cycles per frame for retrace and settling, to project images at 15 Hz refresh rate. 2000 pixels were projected for each of the 250 concentric scan rings at a constant 10 MHz pixel rate, creating an equivalent resolution of 500 lines by 500 pixels, though the limited modulation speed of the laser diode produced some blurring between adjacent pixels. Sample binary red images were projected by the scanning fiber projection display. For these images, a moderate drive voltage (approximately +/−15 V) to the piezoelectric actuator was used in order to produce an approximate 30° throw angle.

The current prototype has demonstrated the equivalent of a 500 line by 500 pixel resolution (250 concentric circles of 2000 pixels each) at a 15 Hz refresh rate. To increase the refresh rate to 30 Hz while maintaining this resolution, the first-mode resonance of the fiber cantilever must be increased from 5 kHz to 10 kHz. The resonant scan rate is a function of the material of the fiber, its radius, and the cantilever length. The relationship of the first and second resonance frequencies (F) of transverse vibration for a cylindrical optical fiber material and physical dimensional properties of a base-excited fixed-free cantilever are expressed in equation 1, below.

$$F = \frac{\pi\sqrt{E}}{16\sqrt{\rho}} R/L^2 (1.194^2, 2.988^2, \ldots) \tag{1}$$

Where ρ=density, E=modulus of elasticity, R=radius, and L=length of solid cylindrical fiber cantilever.

In order to achieve a first-mode resonance of 10 kHz, one may use a custom optical fiber with an 80 um cladding diameter (StockerYale Inc., Salem, N.H.) with a cantilever length of 2.4 mm. Using this method, scanning fiber endoscopes capable of sampling 500 line×500 pixel images at a 30 Hz frame rate were successfully constructed. The decreased fiber cantilever length also allows a reduction in the length of the housing from 13 mm to 9 mm.

With a given first-mode resonance of the scanning fiber, scan lines and frame rate may be traded off with one another. The same 10 kHz first-mode resonance scanner has been used to generate 240-line images at 60 Hz and up to 600-line images at 30 Hz and, by reprogramming the drive electronics, 1000-line images at 15 Hz can also be achieved—approximating HDTV resolution. Such configurability could enable the user to choose a higher resolution mode when projecting still images and a higher frame rate when projecting video. The ultimate resolution limit is determined by the diffraction limit of the lens assembly and the type of optical scanning through the lenses, assuming control of lens aberrations and scan distortions.

In conclusion, a light-scanning engine that is compact and robust was developed. A powerful feature of the scanning fiber technology is its configurability. The resolution, frame rate, and throw angle can be adjusted dynamically to accommodate high resolution still images, high frame rate video presentation, and different screen sizes at variable throw distances.

Fast modulatable laser sources in red, green, and blue colors are key components for the future development of a full-color scanning fiber projection display. Laser diodes can satisfy these requirements for red and blue (e.g., 635 nm Thor Labs Model LPS-635 and 440 nm Nichia Model NDHB510APAEI, respectively). As there are no green laser diodes currently available, a green semiconductor laser, such as those produced by Corning and Novalux may be used. Each laser can be coupled to a single-mode optical fiber and a fiber-optic combiner (e.g., SIFAM Fibre Optics Ltd., 635/532/460 RGB combiner) can be used to form an RGB beam with single-mode properties.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for projecting one or more images onto a surface and obtaining feedback with an optical input-output assembly, the method comprising:
    generating a sequence of light in response to one or more image representations and a scan pattern of an optical fiber;
    articulating the optical fiber in the scan pattern, wherein articulating the optical fiber comprises repeatedly:
        driving the optical fiber along the scan pattern;
        retracing the scan pattern; and
        then settling the optical fiber;
    projecting the sequence of light from the articulated optical fiber to form the one or more images on the surface in a first orientation;
    generating a feedback signal with a sensor; and
    projecting the sequence of light from the articulated optical fiber to form the one or more images on the surface in a second orientation, based on the feedback signal.

2. The method of claim 1, wherein the generating of the feedback signal with the sensor is in response to reflections of the sequence of light.

3. The method of claim 1, wherein the sensor is an orientation sensor and further comprising determining an orientation with the orientation sensor; and
    wherein the generating the feedback signal with the sensor is in response to the determined orientation.

4. The method of claim 3, wherein the orientation sensor is an accelerometer.

5. The method of claim 3, wherein the orientation sensor is a tilt sensor.

6. The method of claim 1, wherein the sequence of light comprises a non-visible wavelength.

7. The method of claim 6, wherein the non-visible wavelength comprises infrared light.

8. The method of claim 1, further comprising generating an input signal to an electronic device in response to the feedback signal.

9. A system for projecting one or more images on a surface and obtaining feedback, the system comprising:
    a projection assembly comprising a light-scanning optical fiber, the projection assembly operable to project a sequence of light from the light-scanning optical fiber onto a surface according to a scan pattern;
    a sensor;
    a laser assembly coupled with the light-scanning optical fiber and operable to generate the sequence of light; and
    a processor coupled with the projection assembly, the sensor, and the laser assembly, the processor comprising a tangible medium, the tangible medium comprising instructions that when executed cause the processor to:
        determine the sequence of light in response to one or more image representations and the scan pattern;
        provide control signals to the laser assembly and the projection assembly to generate and project the sequence of light from the light-scanning optical fiber according to the scan pattern to form the one or more images on the surface, wherein the control signals comprise instructions to repeatedly:
        drive the optical fiber along the scan pattern,
        drive the optical fiber to retrace the scan pattern,
        to settle the optical fiber; and
        receive a feedback signal generated by the sensor;
        adjust the orientation of projection of the sequence of light on the surface from a first orientation to a second orientation based on the feedback signal generated by the sensor.

10. The system of claim 9, wherein the sensor is operable to measure reflections from light projected onto the surface by the light-scanning optical fiber and generate the feedback signal corresponding thereto in response to reflections of the sequence of light.

11. The system of claim 9, wherein the sensor is an orientation sensor operable to measure an orientation and generate the feedback signal corresponding thereto in response to the measured orientation.

12. The system of claim 11, wherein the orientation sensor is operable to measure the orientation of at least a portion of the system.

13. The system of claim 11, wherein the orientation sensor is operable to measure the orientation of the projection assembly.

14. The system of claim 12, wherein the orientation sensor is an accelerometer.

15. The system of claim 12, wherein the orientation sensor is a tilt sensor.

16. The system of claim 9, wherein the sequence of light comprises a non-visible wavelength.

17. The system of claim 16, wherein the non-visible wavelength comprises infrared light.

18. The system of claim 9, the tangible medium comprises instructions that when executed cause the processor to generate an input signal to the projection assembly in response to the feedback signal.

19. The system of claim 12, wherein the tangible medium comprises instructions that when executed cause the processor to generate an input signal to a driver.

20. The system of claim 19, wherein the input signal to the driver is an input signal to a fiber actuator.

* * * * *